April 17, 1956 F. MEILLAND Plant Pat. 1,469
ROSE PLANT
Filed May 16, 1955
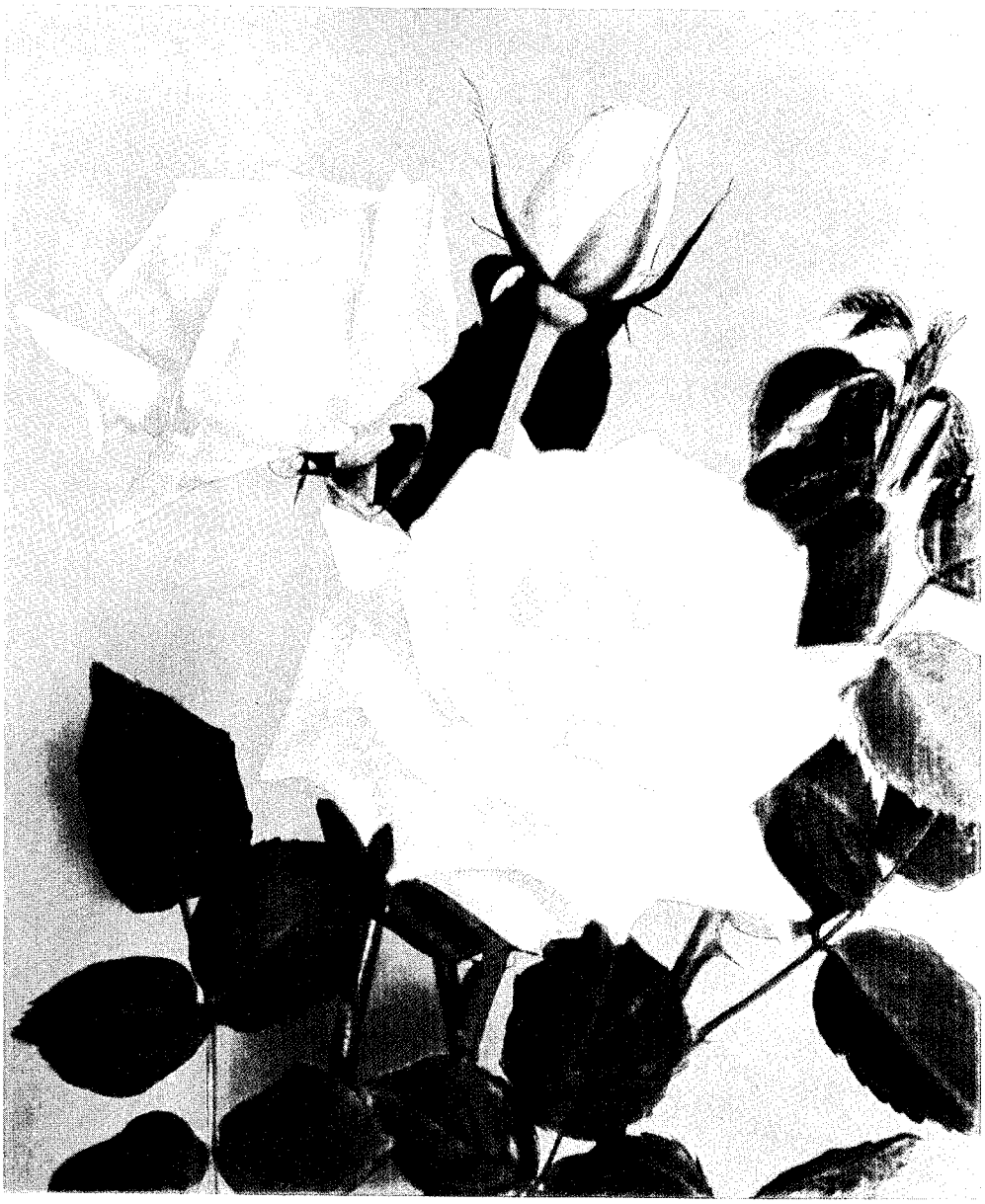
Inventor.
Francis Meilland
By: Cobb & Cobb
Attorneys.

United States Patent Office

Plant Pat. 1,469
Patented Apr. 17, 1956

1,469

ROSE PLANT

Francis Meilland, Cap Azura, Cap d'Antibes, France, assignor to The Conard-Pyle Company, West Grove, Pa., a corporation of Pennsylvania Application May 16, 1955, Serial No. 508,836

Claims priority, application France July 30, 1954

1 Claim. (Cl. 47—61)

The present invention relates to a new and distinct variety of rose plant of the hybrid tea class, which was originated by me by crossing the variety "Mme. Kriloff" (unpatented) with an unnamed and unpatented seedling derived from a cross of the variety "Peace" (Plant Patent No. 591) × "Geneve" (unpatented).

As the result of this cross, I have produced a new variety of rose plant which is particularly characterized as to novelty by the excellent form of its blooms, the firm substance of the flower petals which contributes to the long-lasting qualities of the blooms both on the bush and as cut flowers, and the unusual and distinctive color of the blooms, said color ranging from Buff Yellow to Orange-Pink in general color tonality and is retained throughout the entire life of the blooms.

The foregoing characteristics definitely differentiate the new variety from its parents, as well as from all other varieties of which I am presently aware, and asexual reproduction of the new variety by budding, as performed both in France and at West Grove, Pennsylvania, U. S. A., shows that these characteristics and distinctions come true to form and are estabilshed and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—"Mme. Kriloff."
*Pollen parent.*—An unnamed seedling of "Peace" × "Geneve."
Propagation: Holds its distinguishing characteristics through succeeding propagations by budding.

FLOWER

Locality where grown and observed: West Grove, Pennsylvania, U. S. A.
Flowers borne: Singly to stem; on stems of medium length and normal strength.
Quantity of bloom. Free, outdoors.
Continuity: Continuous.
Fragrance: Moderate.
Bud:
*Peduncle.*—Medium length; medium caliper; stiff; rough; medium number of reddish brown prickles. Color—Light Cress Green, Plate XXXI, sometimes marked with Brick Red, Plate XIII on one side.

*Before calyx breaks.*—Size—medium. Form—medium length; ovoid; with a conspicuous neck; with foliaceous appendages on the surface of the bud; with stout, entire or little-cut bristle-like foliaceous parts extending beyond the tip of the bud equal to ¼ or more of its length.
*As calyx breaks.*—Color—mainly Pinard Yellow, Plate IV, veined and shaded towards tip with Rose Doree, Plate I.
*As first petal opens.*—Size—medium. Form—medium length; ovoid. Color: outside—from Grenadine Pink, Plate II to Strawberry Pink, Plate I at outer edge, shading to Pinard Yellow, Plate IV at base; inside—warm Buff, Plate XV at outer edge, veined with Bittersweet Pink, Plate II, shading to Lemon Chrome, Plate IV at base.
*Opening.*—Opens up well.
Bloom:
*Size (when fully open).*—Medium.
*Petalage.*—Double; from 35 to 48 petals; arranged regularly.
*Form.*—Cupped at first and remaining cupped; outer petals at first being tightly rolled outward and remaining tightly rolled outward at maturity.
Petals: Medium thickness; leathery; with inside velvety and outside satiny.
*Shape.*—Outer petals—obovate; generally with no notches. Intermediate petals—obovate; generally with 1 notch, but sometimes none. Inner petals—obovate; generally with 1 notch.

This description of a newly opened flower was made from a rose grown outdoors in the month of October, at West Grove, Pennsylvania, U. S. A.:

Color:
*Outer petal.*—Outside surface—Strawberry Pink, Plate I, shading to Buff Yellow, Plate IV at base, with veins of Strawberry Pink, Plate I, and with Lemon Chrome, Plate IV at point of attachment. Inside surface—Warm Buff, Plate XV, shading to Light Cadmium, Plate IV at base, with very narrow margin of Peach Red, Plate I towards edge, and with veins marked Strawberry Pink, Plate I.
*Intermediate petal.*—Outside surface—Strawberry Pink, Plate I, shading to Baryta Yellow, Plate IV, with basal margin having a narrow short band of Pale Lemon Yellow, Plate IV. Inside surface—Buff Yellow, Plate IV, shading to Empire Yellow, Plate IV; no prominent veins.
*Inner petal.*—Outside surface—Strawberry Pink, Plate I, shading to Baryta Yellow, Plate IV and then to Pale Lemon Yellow, Plate IV. Inside surface—Pale Orange Yellow, Plate III, shading to Buff Yellow, Plate IV and then to Lemon Chrome, Plate IV at base.

This description was made from a rose that was open for three days outdoors in the month of October, at West Grove, Pennsylvania, U. S. A.:

Color:
*Outer petal.*—Outside surface—Orange Pink, Plate II, shading to Barium Yellow, Plate XVI. Inside surface—Cream Color, Plate XVI, shading to Empire Yellow, Plate IV and then to Wax Yellow, Plate XVI, with Lemon Chrome, Plate IV at base.
*Inner petal.*—Outside surface—Light Ochraceous Salmon, Plate XV, shading to Barium Yellow, Plate XVI, with Strontian Yellow, Plate XVI at base. Inside surface—Buff Yellow, Plate IV, shading to Empire Yellow, Plate IV, with Lemon Chrome, Plate IV at base.

General color effect:

*Newly opened flower.*—Buff Yellow, Plate IV, washed with Strawberry Pink, Plate I on outer petals, and center petals showing a uniform Strawberry Pink, Plate I.

*3-days open.*—Uniformly Buff Yellow, Plate IV, with slight washing of Strawberry Pink, Plate I here and there.

Behavior: Drop off cleanly.

Flower longevity: On bush in garden—4 days in October. Cut roses grown outdoors and kept at living-room temperatures—4 days in October.

REPRODUCTIVE ORGANS

Stamens: Medium number; arranged regularly about pistils.

Filaments: Few without anthers; medium length. Color—Scarlet, Plate I, becoming Light Cadmium, Plate IV.

Anthers: Medium size; all open at once; occasionally an anther fused with a petaloid. Color—Primuline Yellow, Plate XVI.

Pollen: Moderate. Color—gold.

Pistils: Medium number.

Styles: Uneven; medium length; medium caliper; columnar.

Stigma: Color—whitish yellow.

Ovaries: Protruding from calyx.

Hips: None.

Sepals: Permanent; moderately long; spear-shaped.

Seeds: None.

PLANT

Foliage:

*Leaves.*—Compound of 5 leaflets; normal abundance; medium size; leathery.

*Leaflets.*—Shape—oval, with acute apex. Base—round. Margin—simply serrate.

*Color.*—Mature: upper surface—Cedar Green, Plate VI; under surface—Olivine, Plate XXXII, with anastomosing veins of Yellowish Citron, Plate XVI. Young: upper surface—Morocco Red, Plate I, overlaying Courge Green, Plate XVII; under surface—Vindine Green, Plate VI, with veins of Eugenia Red, Plate XIII.

*Rachis (the supporting stem of the compound leaf).*—Medium weight. Upper side—grooved; prickly. Under side—generally smooth.

*Stipules.*—Medium length; medium width; with medium length points turning out at an angle of more than 90°.

*Disease resistance.*—Average resistance to mildew and blackspot as compared with other varieties grown under comparable cultural conditions at West Grove, Pennsylvania, U. S. A.

Growth:

*Habit.*—Bushy; upright; well-branched.

*Growth.*—Vigorous.

*Canes.*—Medium weight.

*Main stems.* — Color — Parrot Green, Plate VI. Thorns—several; medium length; straight; with medium length, oval base. Prickles—none. Hairs—none.

*Branches.* — Color — Parrot Green, Plate VI. Thorns—several; medium length; straight; with medium length, narrow, oval base. Prickles—several. Color—Brazil Red, Plate I. Hairs—none.

*New shoots.* — Color — Brick Red, Plate XIII. Thorns—several; medium length; straight; with medium narrow, oval base. Prickles—none. Hairs—none.

I claim:

A new and distinct variety of rose plant of the hybrid tea class, substantially as herein shown and described, characterized particularly as to novelty by the excellent form of its blooms, the firm substance of the flower petals and the attendant long-lasting qualities of the blooms both on the bush and as cut flowers, and the unusual and distinctive Buff Yellow to Orange Pink general color tonality of the blooms.

No references cited.